United States Patent [19]

Wada

[11] 4,377,171
[45] Mar. 22, 1983

[54] ELECTRONIC THERMOMETER

[75] Inventor: Yoshihiro Wada, Ikoma, Japan

[73] Assignee: Sharp Kabushiki Kaisha, Osaka, Japan

[21] Appl. No.: 236,581

[22] Filed: Feb. 20, 1981

[30] Foreign Application Priority Data

Feb. 23, 1980 [JP] Japan .................................. 55-22097

[51] Int. Cl.³ ............................................. A61B 10/00
[52] U.S. Cl. .................................... 128/736; 128/738
[58] Field of Search ............................... 128/736, 738

[56] References Cited

U.S. PATENT DOCUMENTS 4,031,365 6/1977 Raggiotti et al. .................... 128/736
4,151,831 5/1979 Lester .............................. 128/738 X Primary Examiner—Kyle L. Howell
Assistant Examiner—John C. Hanley
Attorney, Agent, or Firm—Birch, Stewart, Kolasch and Birch

[57] ABSTRACT

An electronic thermometer suited for measuring a basal body temperature comprises a current time information keeping circuit. A time preset system is included in the electronic thermometer so that a desired time at which the body temperature measuring operation should be performed is preset in the electronic thermometer. When the current time reaches the preset time, the body temperature measuring operation is automatically conducted, and the measured data is stored in a memory means. A digital display unit is associated with the memory means so that the measured body temperature stored in the memory means is displayed on the digital display unit at any time.

3 Claims, 3 Drawing Figures

ELECTRONIC THERMOMETER

BACKGROUND AND SUMMARY OF THE INVENTION

The present invention relates to an electronic thermometer and, more particularly, to an electronic woman thermometer for automatically detecting a basal body temperature.

The basal body temperature information is effective for birth control. However, it is not widely used because of difficulty in obtaining accurate readings. That is, the basal body temperature must be read or detected everyday at the same time. More specifically, the temperature detection must be conducted after the woman wakes up but before she gets up. Moreover, the detection operation must be conducted for more than five minutes. Therefore, the basal body temperature method is not widely used even though the basal body temperature information provides important data.

Accordingly, an object of the present invention is to provide an electronic thermometer for automatically conducting the basal body temperature detection at a preselected time.

Another object of the present invention is to facilitate basal body temperature detection.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

A typical construction of a conventional electronic thermometer suited for detecting basal body temperature is disclosed in British Patent Laid Open Specification No. 2,045,480, ELECTRONIC WOMAN THERMOMETER, published on Oct. 29, 1980 and assigned to the same assignee as the present application.

To achieve the above objects, pursuant to an embodiment of the present invention, a time information keeping circuit is incorporated in an electronic thermometer. A desired detection time is preset in the electronic thermometer so that the temperature detection operation is automatically conducted at the desired preselected time. The detected temperature information is stored in a memory system of which contents are displayed on a digital display panel at any time.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
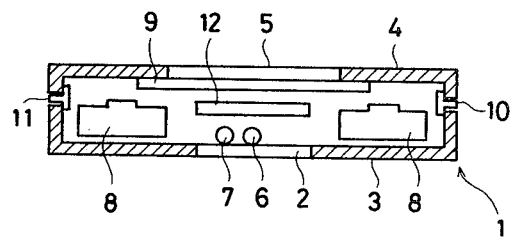
FIG. 1 is a sectional view of an embodiment of an electronic thermometer of the present invention.

The electronic thermometer of the present invention comprises a flat shaped housing 1 suited for attaching to a desired portion of a body of a person to be measured. A first major surface of the housing 1 comprises a portion 2 made of a material showing a high thermal conductivity, and another portion 3 made of a material showing a low thermal conductivity. A second major surface of the housing 1 comprises a portion 4 made of a material showing a low thermal conductivity, and a transparent wall 5.

A temperature sensor 6 is disposed in the flat shaped housing 1 so that the temperature sensor 6 makes contact with the portion 2 made of the material showing the high thermal conductivity. A capacitor 7 is disposed near the temperature sensor 6. The capacitor 7 functions to determine the time constant of an oscillation circuit included in a body temperature measuring system. Power supply cells 8 are disposed in the housing 1 to supply power to the elements included in the housing 1. A liquid crystal display panel 9 is disposed in the housing 1 in a manner to confront the transparent wall 5. The electronic thermometer further comprises a measuring time preset switch 10, a current time information adjusting switch 11, and an LSI 12 for controlling the operation of the electronic thermometer.

The LSI 12 is a C-MOS LSI for ensuring a continuous operation for more than one year when a silver oxide cell is employed.

Figure 2:
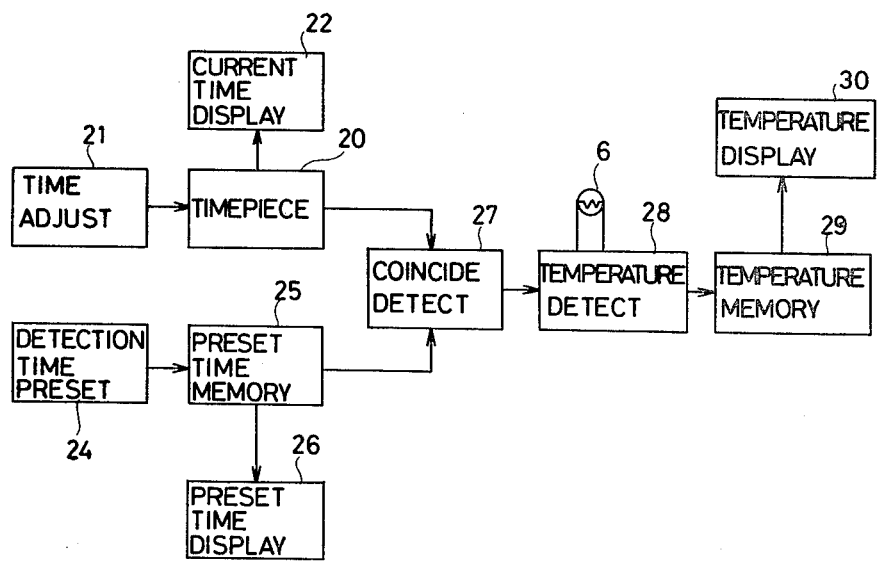
FIG. 2 is a block diagram of the electronic thermometer of FIG. 1.

FIG. 2 is a block diagram schematically showing a circuit construction of the electronic thermometer of FIG. 1.

A current time information keeping circuit 20 is included in the electronic thermometer of the present invention to store the current time information. A time adjust circuit 21 is associated with the current time information keeping circuit 20 for adjusting the current time information stored in the current time information keeping circuit 20. A current time information display unit 22 is connected to the current time information keeping circuit 20 for displaying the current time information. That is, the current time information keeping circuit 20, the time adjust circuit 21, and the current time information display unit 22 function, in combination, as a digital timepiece.

A measuring time preset circuit 24 is associated with the measuring time preset switch 10 for presetting a desired time at which the body temperature measuring operation should be performed. The preselected preset time information derived from the measuring time preset circuit 24 is introduced into and stored in a preset time memory 25. The preset time information stored in the preset time memory 25 is displayed on a preset time information display unit 26.

The contents stored in the current time information keeping circuit 20 and the preset time memory 25 are introduced into a coincide detection circuit 27 which develops a detection output to the following temperature measuring circuit 28 when the contents stored in the current time information keeping circuit 20 become identical with the contents stored in the preset time memory 25. The temperature measuring circuit 28 performs the body temperature measuring operation in accordance with an output signal derived from the temperature sensor 6 when the detection output is derived from the coincide detection circuit 27. The body temperature data obtained in the temperature measuring circuit 28 is applied to and stored in a body temperature memory 29. The body temperature stored in the body temperature memory 29 is displayed on a body temperature display unit 30.

When, for example, 5:00 a.m. is preset in the preset time memory 25, and the user attaches the electronic thermometer to a desired portion of her body and goes to bed, the basal body temperature measuring operation is automatically conducted at 5:00 a.m. in the next morning even when she is still sleeping. The measured data is stored in the body temperature memory 29, and displayed on the body temperature display unit 30. Therefore, the basal body temperature data can be observed after she gets up.

Figure 3:
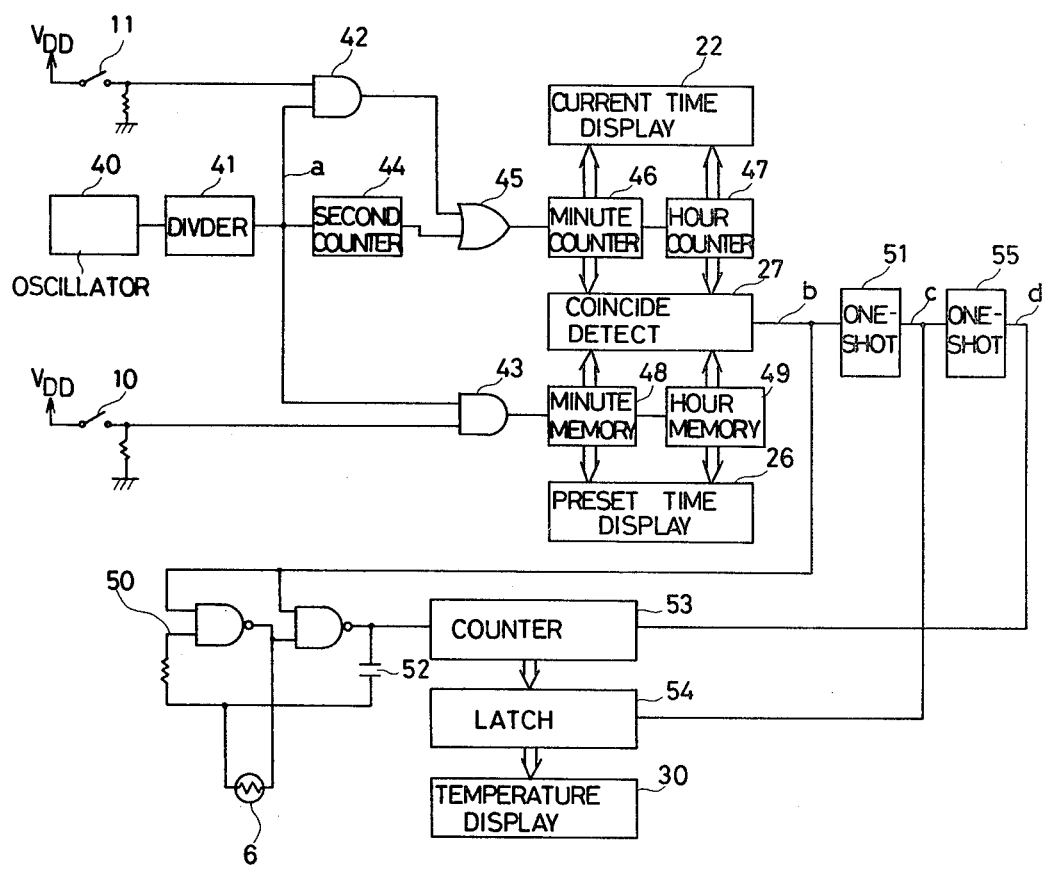
FIG. 3 is a further detailed block diagram of the electronic thermometer of FIG. 1.

FIG. 3 shows the circuit construction of the electronic thermometer in detail. Like elements corresponding to those of FIGS. 1 and 2 are indicated by like numerals.

An oscillator circuit 40 is provided for developing a base frequency signal to the following frequency divider 41. The frequency divider 41 develops a one second signal "a" of one hertz. The one second signal "a" is applied to one input terminal of an AND gate 42, to one input terminal of another AND gate 43, and to a second information counter 44 of radix sixty. The second information counter 44 develops a one minute signal which is applied to a minute information counter 46 of radix sixty through an OR gate 45. The minute information counter 46 develops a one hour signal which is applied to an hour information counter 47 of radix twenty-four. Accordingly, the counters 44, 46 and 47 store the current time information. The contents stored in the minute information counter 46 and the hour information counter 47 are adjustable through the use of the current time information adjusting switch 11. More specifically, as long as the current time information adjusting switch 11 is actuated, the one second signal "a" is introduced into the minute information counter 46 via the AND gate 42 and the OR gate 45 to advance the information stored in the minute information counter 46 and the hour information counter 47.

The current time information stored in the minute information counter 46 and the hour information counter 47 is applied to the current time information display unit 22 for displaying the current time information. The contents stored in the minute information counter 46 and the hour information counter 47 are further applied to the coincide detection circuit 27. The coincide detection circuit 27 is connected to further receive the preset time information stored in a minute information preset memory 48 of radix sixty and an hour information preset memory 49 of radix twenty-four. The measuring time preset switch 10 is connected to the AND gate 43 so that the one second signal "a" is introduced into the minute information preset memory 48 (counter) as long as the measuring time preset switch 10 is actuated. The preset measuring time stored in the minute information preset memory 48 (counter of radix sixty) and the hour information preset memory 49 (counter of radix twenty-four) is applied to the preset time information display unit 26 for confirmation purposes.

When the current time reaches the preset time stored in the minute information preset memory 48 and the hour information preset memory 49, the coincide detection circuit 27 develops the detection output "b". The detection output "b" is held before the contents stored in the minute information counter 46 change, namely, for one minute. In response to the detection output "b", an oscillator circuit 50 is enabled, and a one-shot multivibrator 51 is enabled. More specifically, at the leading edge of the detection output "b", the oscillator circuit 50 begins the oscillation of which frequency is determined by a time constant determined by a capacitor 52 and the temperature sensor 6. At the trailing edge of the detection output "b", namely, one minute later, the one-shot multivibrator 51 develops a pulse signal "c".

The oscillator circuit 50 is connected to a counter 53 which counts the oscillation times during one minute. The thus obtained count information stored in the counter 53 is transferred to and stored in a latch circuit 54 in response to the development of the pulse signal "c". The count information, representative of the measured body temperature, stored in the latch circuit 54 is displayed on the body temperature display unit 30. In response to the trailing edge of the pulse signal "c", another one-shot multivibrator 55 is operated to develop a pulse signal "d" for clearing the counter 53. The capacitance of the capacitor 52, and the characteristics of the temperature sensor 6 are selected so that the oscillation times of the oscillator circuit 50 in one minute corresponds to the temperature detected by the temperature sensor 6.

When the measuring range extends over a wide range, it is preferable that a converter circuit is disposed between the latch circuit 54 and the body temperature display unit 30. The above-mentioned current time information display unit 22, the preset time information display unit 26, and the body temperature display unit 30 are included in the liquid crystal display panel 9.

A typical construction for measuring the basal body temperature is disclosed in British patent publication No. 2,045,480 published on Oct. 29, 1980, and assigned to the same assignee as the present application.

The invention being thus described, it will be obvious that the same may be varied in many ways. Such variations are not to be regarded as a departure from the spirit and scope of the invention, and all such modifications are intended to be included within the scope of the following claims.

What is claimed is:
1. An electronic thermometer comprising:
temperature measuring means for measuring a body temperature,
said temperature measuring means comprising a temperature sensor probe, an oscillator circuit of which the oscillation frequency is a function of the output signal derived from said temperature sensor probe and counter means for counting said oscillation frequency of said oscillator circuit which is a measure of said body temperature;
time information keeping means for storing current time information;
preset time memory means for storing a preselected time data at which the body temperature measuring operation is to be performed;
coincide detection means for developing a coincide detection output when the current time information stored in said time information keeping means becomes identical with said preselected time data stored in said preset time memory means;
drive means for activating said temperature measuring means when said coincide detection output is developed from said coincide detection means;
temperature memory means for storing a measured temperature derived from said temperature measuring means in response to said coincide detection output derived from said coincide detection means; and a temperature display unit for displaying said measured temperature stored in said temperature memory means, said temperature memory means comprising a latch circuit for storing the count information relayed from said counter means, said count information representing a function of the body temperature for display on said body temperature display unit, whereby the temperature measuring means performs the body temperature measuring operation via said temperature sensor probe automatically in response to said output signal derived from said temperature sensor when said coincide detection output signal is received from said coincide detection means, the body temperature data obtained in said temperature measuring means being applied to and stored in said temperature memory means for display on said temperature display unit.

2. The electronic thermometer of claim 1, wherein said drive means comprises a one-shot multivibrator for activating said oscillator circuit for a predetermined period of time after generation of said coincide detection output derived from said coincide detection means.

3. The electronic thermometer of claim 1, wherein said current time information display unit, said preset time information display unit and said body temperature display unit are included in a liquid crystal display panel.

* * * * *